US010123680B2

(12) United States Patent
Park et al.

(10) Patent No.: US 10,123,680 B2
(45) Date of Patent: Nov. 13, 2018

(54) OPERATION CONTROL SYSTEM OF CAPSULE TYPE ENDOSCOPE, AND CAPSULE TYPE ENDOSCOPE SYSTEM COMPRISING SAME

(71) Applicant: INDUSTRY FOUNDATION OF CHONNAM NATIONAL UNIVERSITY, Gwangju (KR)

(72) Inventors: Suk Ho Park, Gwangju (KR); Jong Oh Park, Gyeonggi-do (KR); Cheong Lee, Gwangju (KR); Hyun Chul Choi, Jeollanam-do (KR); Semi Jeong, Jeollabuk-do (KR)

(73) Assignee: Industry Foundation of Chonnam National University, Gwangju (KR)

( * ) Notice: Subject to any disclaimer, the term of this patent is extended or adjusted under 35 U.S.C. 154(b) by 340 days.

(21) Appl. No.: 14/646,542

(22) PCT Filed: Nov. 13, 2013

(86) PCT No.: PCT/KR2013/010271
§ 371 (c)(1),
(2) Date: May 21, 2015

(87) PCT Pub. No.: WO2014/081150
PCT Pub. Date: May 30, 2014

(65) Prior Publication Data
US 2015/0297065 A1  Oct. 22, 2015

(30) Foreign Application Priority Data
Nov. 23, 2012  (KR) .................. 10-2012-0133515

(51) Int. Cl.
*A61B 1/00* (2006.01)
*A61B 1/04* (2006.01)

(52) U.S. Cl.
CPC ...... *A61B 1/00158* (2013.01); *A61B 1/00016* (2013.01); *A61B 1/041* (2013.01)

(58) Field of Classification Search
CPC . A61B 1/041; A61B 5/6861; A61B 2562/162; A61B 1/00158;
(Continued)

(56) References Cited

U.S. PATENT DOCUMENTS

2008/0272873 A1  11/2008  Reinschke et al.
2011/0213205 A1   9/2011  Uchiyama et al.
(Continued)

FOREIGN PATENT DOCUMENTS

CN      1718152 A   1/2006
CN    101623190 A   1/2010
(Continued)

OTHER PUBLICATIONS

A. Chiba et al., Magnetic Actuator for Capsule Endoscope Navigation System, IEEE, 2005 FC 10.
(Continued)

*Primary Examiner* — John P Leubecker
*Assistant Examiner* — Pamela F Wu
(74) *Attorney, Agent, or Firm* — Rabin & Berdo, P.C.

(57) ABSTRACT

The present invention relates to an operation control system for spirally operating a capsule endoscope along a tubular organ, and a capsule type endoscope system comprising the same. The operation control system for a capsule endoscope of the present invention comprises: a magnetic field generation portion (100) comprising a first coil unit (110) provided on three orthogonal axes to generate a magnetic field and a second coil unit (120) comprising one coil structure for generating a magnetic field gradient; and a mechanical coil driving portion (130) for three-dimensionally rotating the second coil unit (120), thereby generating a rotating mag-
(Continued)

netic field and the magnetic field gradient. Therefore, it is possible to simplify the operation control system for a capsule endoscope by forming the rotating magnetic field and the magnetic field gradient for a spiral motion of a capsule endoscope only with a minimum coil system.

8 Claims, 7 Drawing Sheets

(58) Field of Classification Search
CPC ............ A61B 2034/2051; A61B 34/73; A61B 2034/731–2034/733; A61B 1/00131; A61B 1/00133; A61B 1/00147; A61B 1/00149; A61B 1/0016; A61B 1/01; A61M 25/0158
USPC .......................................... 600/37, 422, 424
See application file for complete search history.

(56) References Cited

U.S. PATENT DOCUMENTS

| | | | |
|---|---|---|---|
| 2011/0301497 A1 | 12/2011 | Shachar et al. | |
| 2011/0316656 A1 | 12/2011 | Reinschke | |
| 2012/0126808 A1* | 5/2012 | Knopp | A61B 5/0515 324/301 |
| 2012/0149981 A1* | 6/2012 | Khait | A61B 1/00158 600/109 |

FOREIGN PATENT DOCUMENTS

| | | |
|---|---|---|
| CN | 101940474 A | 1/2011 |
| CN | 102355866 A | 2/2012 |
| EP | 2 143 368 A1 | 1/2010 |
| JP | 2006-271520 A | 10/2006 |
| JP | 2007-236962 A | 9/2007 |
| JP | 2010-017555 A | 1/2010 |
| JP | 2012-520161 A | 9/2012 |
| KR | 10-2009-0109818 A | 10/2009 |
| KR | 10-2010-0136206 A | 12/2010 |
| KR | 10-2011-0049842 A | 5/2011 |
| RU | 80326 U1 | 2/2009 |
| WO | WO 2008/032815 A1 | 3/2008 |
| WO | WO 2011/118253 A1 | 9/2011 |
| WO | WO 2012/090197 A1 | 7/2012 |

OTHER PUBLICATIONS

European Search Report dated Jul. 14, 2016.
Russian Office Action dated Nov. 10, 2016.
Second Chinese Office Action dated Oct. 24, 2016.
Chinese Office Action dated Mar. 31, 2016.
European Office Action dated Jul. 11, 2017.
Japanese Office Action dated Jun. 7, 2016.

* cited by examiner

OPERATION CONTROL SYSTEM OF CAPSULE TYPE ENDOSCOPE, AND CAPSULE TYPE ENDOSCOPE SYSTEM COMPRISING SAME

TECHNICAL FIELD

The present invention relates to an operation control system of a capsule type endoscope and a capsule type endoscope system comprising the same, and more particularly, to an operation control system of a capsule type endoscope and a capsule type endoscope system comprising the same in which a capsule endoscope is driven to move along a tubular organ by a spiral motion, thereby being capable of making an accurate diagnosis of the wall of the tubular organ.

BACKGROUND ART

A conventional flexible streamlined endoscope is inserted through a mouth or anus and controlled to diagnose ulcerative diseases of the inner wall of the digestive organs, and it causes a patient's suffering. To solve the problem, a capsule endoscope, which has a form to easily enter into the digestive organs through the mouth and takes pictures of the inside of the digestive organs moves the inside of the digestive organs while moving the inside of the digestive organs by peristalsis of the digestive organs in order to make a diagnosis, has been developed.

However, such a capsule endoscope has several disadvantages in that it is difficult to make an accurate diagnosis due to a passive movement by the peristalsis, and in that the capsule endoscope has a limited size because it must be inserted through the mouth so that it is difficult to mount various functional devices on the capsule endoscope.

To solve these disadvantages, researches on an actuation mechanism for actuating the capsule endoscope using an electromagnetic actuation system have been conducted.

Meanwhile, coil systems for actuating such a capsule endoscope have been proposed. For instance, U.S. Patent Publication No. 2008/0272873 (hereafter, "prior art document") discloses a coil system for actuating a capsule endoscope. In U.S. Patent Publication No. 2008/0272873, a total of 18 coils can be used to move the capsule endoscope in a certain direction.

However, the prior art coil system has a problem in that power consumption could be increased to move the capsule endoscope due to a high number of coils and each coil's role is not clearly defined.

DISCLOSURE

Technical Problem

Accordingly, the present invention has been made in an effort to solve the above-mentioned problems occurring in the prior arts, and it is an object of the present invention to provide an operation control system of a capsule type endoscope and a capsule type endoscope system comprising the same in which a capsule endoscope is driven to spirally move along a tubular organ to obtain image information, thereby being capable of making an accurate diagnosis of the wall of the tubular organ.

It is another object of the present invention to provide an operation control system of a capsule type endoscope and a capsule type endoscope system comprising the same which can create a rotating magnetic field and a gradient magnetic field applied from the outside just by the minimum configuration of a coil system in order to realize a spiral motion of the capsule type endoscope, thereby simplifying the configuration of the entire system and being capable of making actuation control of the capsule type endoscope easy.

It is a further object of the present invention to provide an operation control system of a capsule type endoscope and a capsule type endoscope system comprising the same which can make a spiral motion along the tubular organ by interaction between the rotating magnetic field and the gradient magnetic field generated from the outside.

Technical Solution

To achieve the above objects, in an aspect of the present invention, the present invention provides an operation control system of a capsule type endoscope including: a first coil unit having coil portions which are fixed to three axes being at right angles to each other and generate magnetic fields in orthogonal axis directions, respectively; a second coil unit which is disposed to generate a gradient magnetic field in any direction relative to the magnetic field generated by the first coil unit; a coil driving portion for driving the second coil unit to adjust the orientation of the gradient magnetic field; and a control unit including an image receiver which receives an image signal transmitted from a capsule endoscope and a control portion coil controller which controls electric currents supplied to the first and second coil units to adjust the generated magnetic field and controls operation of the coil driving portion.

Preferably, in the present invention, the coil driving portion controls the second coil unit to perform three-dimensional rotation by independent biaxial rotations.

Preferably, in the present invention, each coil portion of the first coil unit includes a Helmholtz coil.

Preferably, in the present invention, the second coil unit includes a Maxwell coil.

In another aspect of the present invention, the present invention provides a capsule type endoscope system including a capsule endoscope which has magnetization inclined within a range of an acute angle ($0<\delta<90°$) relative to the length direction of the housing of the endoscope and includes a camera module to capture an image and transmit the image to the outside.

In a further aspect of the present invention, the present invention provides a capsule endoscope which is capable of carrying out movement by a spiral motion along the inside of a tubular organ by a rotating magnetic field and a gradient magnetic field generated from the outside, the capsule endoscope having magnetization inclined within a range of an acute angle ($0<\delta<90°$) relative to the length direction of the housing of the endoscope and being capable of capturing an image and transmitting the image to the outside.

Advantageous Effects

As described above, the capsule type endoscope system according to the present invention can form the rotating magnetic field and the gradient magnetic field for the spiral motion of the capsule type endoscope just by the minimum coil system including: the magnetic field forming portion which has the first coil unit disposed on three orthogonal axes to generate a magnetic field and a second coil unit having one coil structure for generating a gradient magnetic field; and a mechanical coil driving portion for three-dimensionally rotating the second coil unit to create the rotating magnetic field and the gradient magnetic field so that the rotating magnetic field and the gradient magnetic field are formed just by the minimum coil system, thereby simplifying the operation control system of the capsule type endoscope.

Additionally, the capsule type endoscope according to the present invention has magnetization characteristics to spirally move along the inside of the tubular organ by the rotating magnetic field and the gradient magnetic field generated from the outside.

EXPLANATION OF REFERENCE NUMERALS IN DRAWINGS

- 110: first coil unit
- 111: x-axis coil portion
- 112: y-axis coil portion
- 113: z-axis coil portion
- 120: second coil unit
- 130: coil driving portion
- 131: vertical post
- 132: rotating arm
- 133: movable arm
- 200: control unit
- 210: image receiver
- 220: coil controller
- 300: capsule endoscope
- 301: housing
- 310: permanent magnet
- 320: camera module
- 330: data transmission module
- 340: power supply module

MODE FOR INVENTION

It should be appreciated that specific structures or functional explanations proposed in example embodiments of the present invention are to describe embodiments according to the concepts of the present invention and may be executed in various forms according to the concepts of the present invention. It should be understood, however, that there is no intent to limit example embodiments of the invention to the particular forms disclosed, but on the contrary, example embodiments of the invention are to cover all modifications, equivalents, and alternatives falling within the technical idea and scope of the present invention.

It will be further understood that the words or terms used in the present invention are used to describe specific embodiments of the present invention and there is no intent to limit the present invention. The singular form of the components may be understood into the plural form unless otherwise specifically stated in the context. It should be also understood that the terms of 'include' or 'have' in the specification are used to mean that there are characteristics, numbers, steps, operations, components, parts, or combinations of the steps, operations, components and parts described in the specification and there is no intent to exclude existence or possibility of other characteristics, numbers, steps, operations, components, parts, or combinations of the steps, operations, components and parts.

Hereinafter, reference will be now made in detail to the preferred embodiment of the present invention with reference to the attached drawings.

Figure 1:
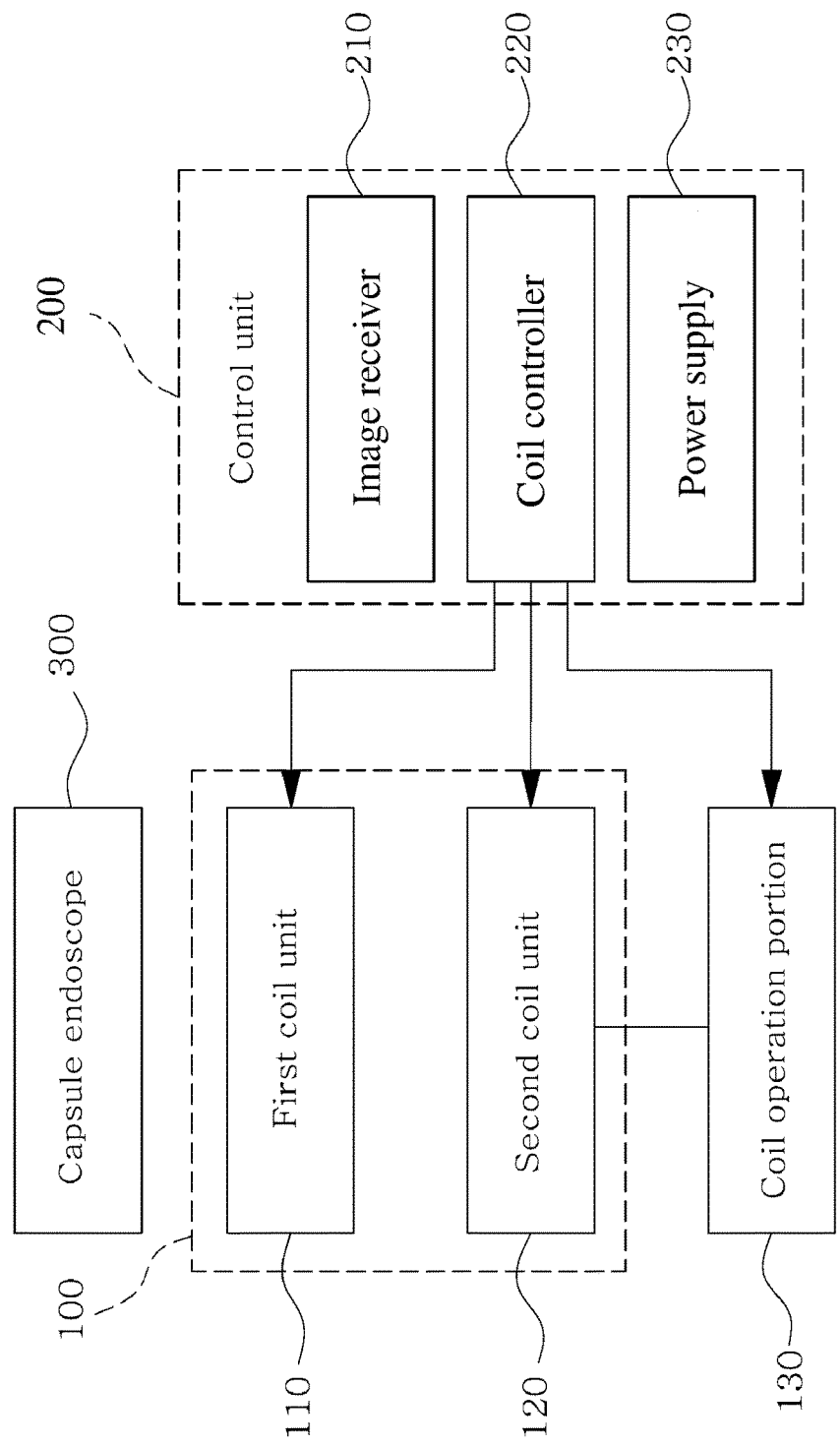
FIG. 1 is a view showing the configuration of a capsule type endoscope system according to a preferred embodiment of the present invention.

Referring to FIG. 1, an operation control system of a capsule type endoscope according to a preferred embodiment of the present invention includes first and second coil units 110 and 120, a coil driving portion 130 for rotating the second coil unit 120 three-dimensionally, and a control unit 200 for receiving information transmitted from a capsule endoscope 300 and controlling power supply applied to the first and second coil units 110 and 120 to control a motion of the capsule endoscope 300 by a magnetic field.

The operation control system of the capsule type endoscope according to the present invention can perform precession of the capsule endoscope 300 by a rotating magnetic field generated by the first coil unit 110 and a spiral motion that is carried out in contiguity with a tube wall when the capsule endoscope 300 moves along the tubular digestive organ using momentum by a gradient magnetic field generated by the second coil unit 120. Hereinafter, each component will be described.

The capsule endoscope 300 is controlled wirelessly by a magnetic field generated from a magnetic field generating portion 100 which includes the first and second coil units 110 and 120.

Figure 2:
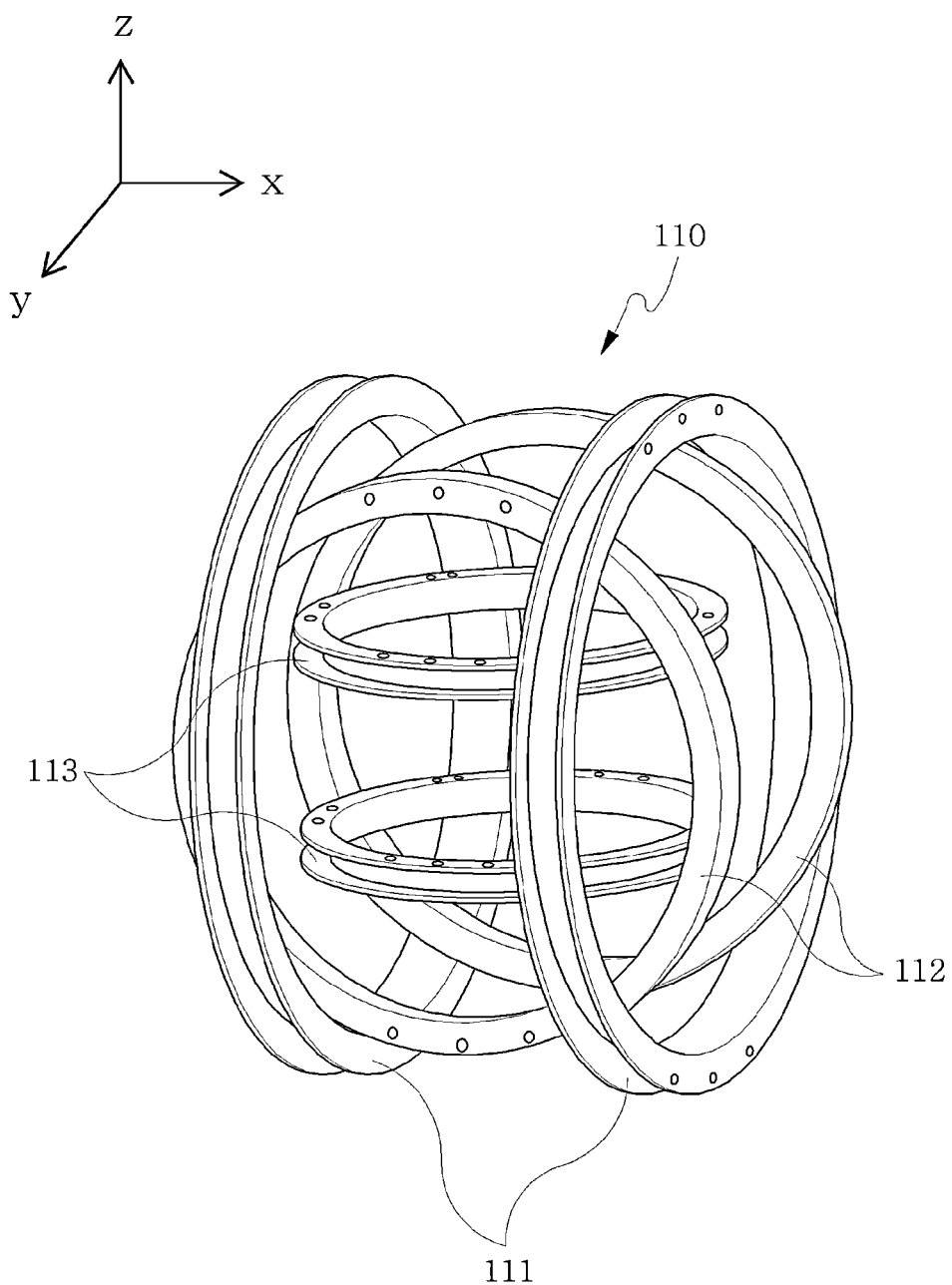
FIG. 2 is a view showing a first coil unit of the capsule type endoscope system according to the preferred embodiment of the present invention.

As shown in FIG. 2, the first coil unit 110 has coil portions 111, 112 and 113 which are respectively fixed to three axes being at right angles to each other and which can generate magnetic fields in orthogonal axis directions.

Not shown in the drawings, but it should be understood that supporting structures may be mounted to respectively fix the coil portions.

The coil portions 111, 112 and 113 may respectively be an x-axis coil portion 111, an y-axis coil portion 112 and a z-axis coil portion, and basically, each of the coil portions 111, 112 and 113 may be provided by a coil structure which can generate a uniform magnetic field, a rotating magnetic field or a gradient magnetic field in a certain direction depending on sizes and directions of applied electric current.

For example, Helmholtz coils or Maxwell coils may be used.

Two Helmholtz coils form a pair. The two Helmholtz coils are spaced apart from each other as long as a radius on the central axis and can generate a uniform magnetic field when electric currents of the same size and direction are applied to the two coils.

In the meantime, the Helmholtz coils can generate the uniform magnetic field depending on sizes or directions of electric currents applied to the two Helmholtz coils. Alternatively, combination of three Helmholtz coils may generate a rotating magnetic field, and it has been disclosed in Korean Patent No. 10-1128034 which has been granted on Mar. 12, 2012 and filed by the same applicant of the present invention application.

Two Maxwell coils form a pair. The two coils have a specific arrangement to generate a uniform gradient magnetic field when electric currents of the same size are applied to the two coils in the opposite directions.

Meanwhile, preferably, the first coil unit 110 uses the Helmholtz coils which are easy to be arranged on three axes to be at right angles to each other. FIG. 2 illustrates the first coil unit having the Helmholtz coils.

As described above, the three coil portions 111, 112 and 113 which are respectively fixed on the three axes to generate the uniform magnetic field can generate a rotating magnetic field depending on sizes and directions of electric currents applied to each coil portion and can induce precession of the capsule endoscope using the rotating magnetic field, and it will be described in detail later.

Figure 3:
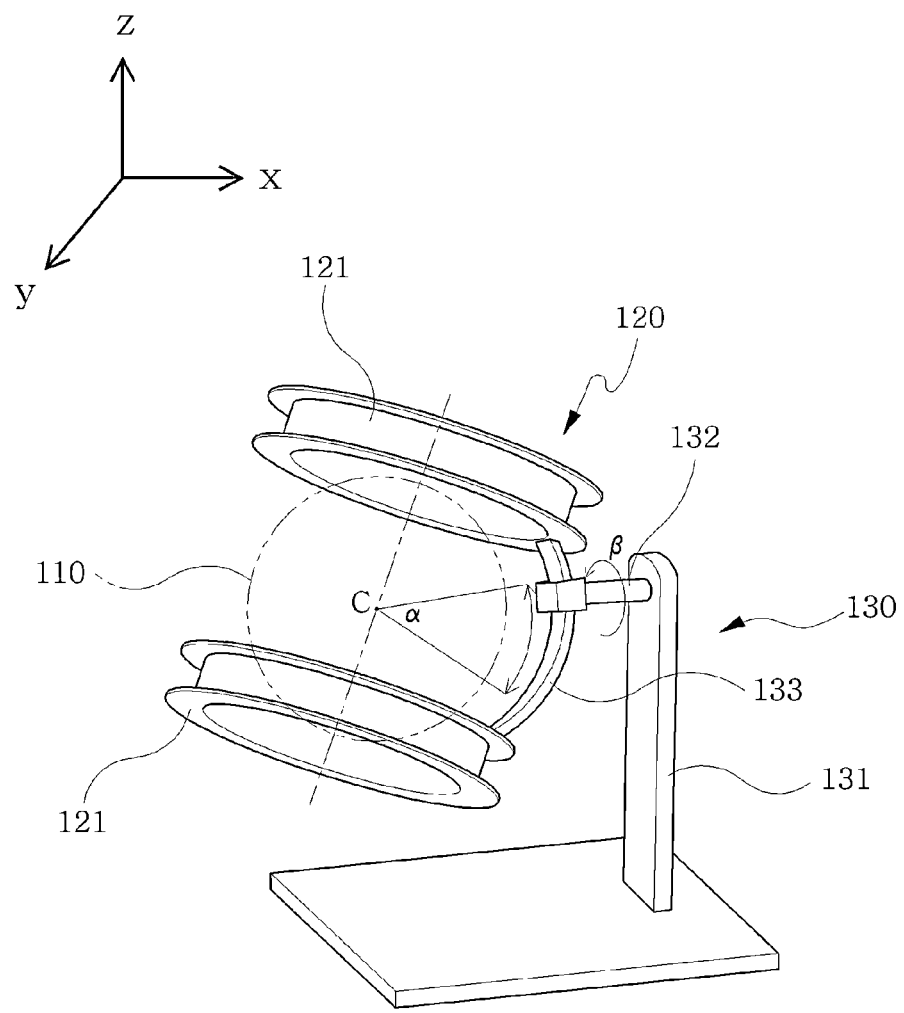
FIG. 3 is a view showing a second coil unit and a coil driving portion of the capsule type endoscope system according to the preferred embodiment of the present invention.

FIG. 3 shows a preferred example of the second coil unit which can generate the gradient magnetic field, and the second coil unit is configured by coils which can generate the gradient magnetic field in one axis direction.

A pair of two coils which are arranged side by side form the coil unit for generating the gradient magnetic field. When electric currents applied to the two coils are in the opposite directions, the gradient magnetic field is generated. In the present invention, the second coil unit, preferably, uses the Maxwell coils.

As shown in FIG. 3, the second coil unit 120 has a pair of the Maxwell coils 121, and the Maxwell coils 121 surround the first coil unit 110.

A gradient magnetic field is formed in the central axis direction of the Maxwell coils 121, and a gradient magnetic field which has an approximately linear slope is formed at the central portion.

The second coil unit 120 has the coil driving portion 130 disposed as a mechanical structure which is capable of three-dimensionally driving with the first coil unit 110 as the center.

The coil driving portion 130 can rotate the second coil unit 120 in certain two directions α and β, and hence, can control the direction of the gradient magnetic field generated from the second coil unit 120 into an arbitrary direction.

Particularly, the second coil unit 120 which provides momentum for translation of the capsule endoscope uses just one coil structure and the direction of the gradient magnetic field can be adjusted using the coil driving portion 130 which can rotate the second coil unit 120 three-dimensionally, so that the present invention can simplify the entire structure of the coil operation system for operating the capsule endoscope.

As shown in FIG. 3, the coil driving portion 130 includes: a vertical post 131 which is vertically fixed on the ground; a rotating arm 132 which is horizontally disposed on the vertical post 131 to be able to rotate; and a movable arm 133 which fixes and supports the second coil unit 120 and is supported at the front end of the rotating arm 132 so as to be able to move vertically.

Actuators, such as motors, which have been known, are mounted at the rotating arm 132 which is rotatable on the vertical post 131 and the movable arm 133 which is vertically movable at the front end of the rotating arm 132 so that the present invention can make an accurate operation control by electronic, hydraulic or pneumatic signals applied from the outside.

Preferably, the movable arm 133 has an arc shape with a proper radius of curvature that makes the second coil unit 120 rotate three-dimensionally on the center of the second coil unit 120 which coincides with the center of the first coil unit and is a virtual rotation axis.

As described above, the coil driving portion 130 can achieve the three-dimensional rotation because the second coil unit 120 can carry out biaxial rotation. Accordingly, the gradient magnetic field direction of the second coil unit 120 can be adjusted arbitrarily.

In this embodiment, the coil driving portion has a gimbal structure capable of carrying out the biaxial rotation, but the present invention is not limited to the above and can use various mechanical devices within the scope that the second coil unit 120 can carry out the rotating motion three-dimensionally, such as a parallel mechanism (Stewart platform) or a robot arm.

Figure 4:
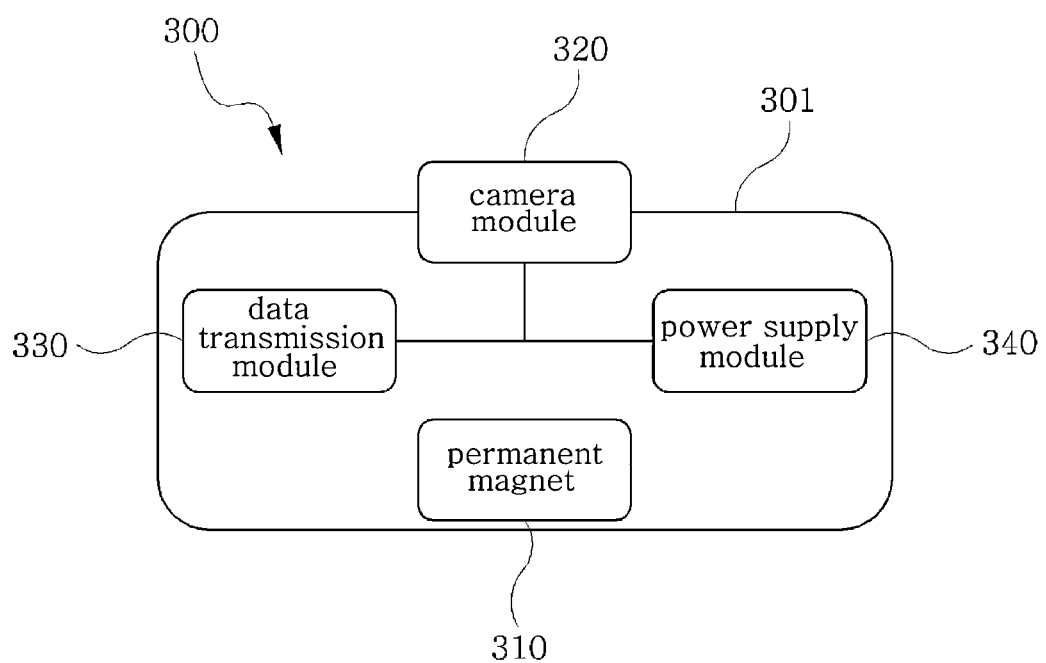
FIG. 4 is a view showing a capsule endoscope of the capsule type endoscope system according to the preferred embodiment of the present invention.

FIG. 4 shows the configuration of the capsule endoscope. The capsule endoscope 300 has a housing 301 which forms the outward appearance, and a permanent magnet 310, a camera module 320, a data transmission module 330 and a power supply module 340 can be accommodated in the housing 301.

The permanent magnet 310 forms magnetization in an arbitrary direction and provides a driving force of the capsule endoscope 300 by interaction with an external magnetic field.

The camera module 320 is to obtain image information, and can be fixed and mounted on the front face, rear face or lateral face of the housing 301. In the meantime, in order to obtain accurate image information inside a living body through the camera module 320, a lighting device may be added.

The data transmission module 330 serves to transmit the image information obtained from the camera module 320 to the outside.

The power supply module 340 supplies actuating power necessary for the lighting device, and such a power supply module 340 can be provided by a battery.

Figure 5:
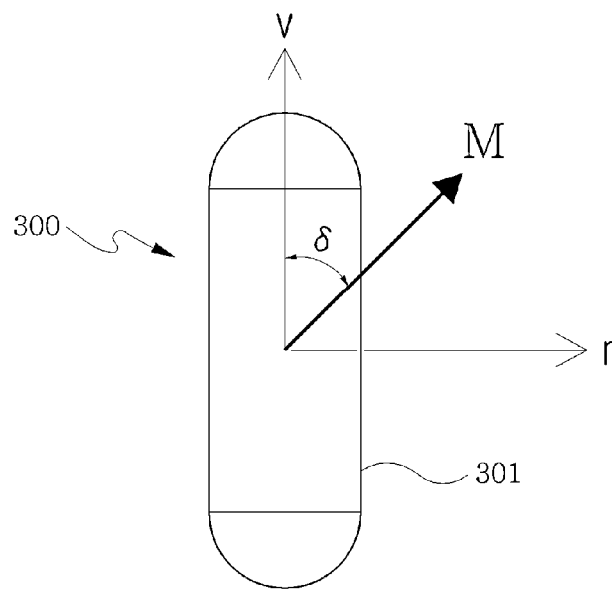
FIGS. 5 and 6(a) and 6(b) are views showing a magnetization configuration of the capsule endoscope of the capsule type endoscope system according to the preferred embodiment of the present invention.

FIG. 5 is a schematic diagram showing an outward appearance of the capsule endoscope. The capsule endoscope has an approximately elongated cylindrical shape and has a slope of a fixed angle δ in the length direction v and the magnetization direction M. Preferably, the magnetization direction M of the capsule endoscope 300 makes an acute angle (0<δ<90°) with the length direction v.

It will be described in more detail later, but in the event that the magnetization direction coincides with the length direction, precession of the capsule endoscope by the external rotating magnetic field is not carried out. In the event that the magnetization direction is perpendicular to the length direction, the capsule endoscope can carry out just precession at a stabilized position and cannot carry out translation by the external gradient magnetic field.

Figure 6:
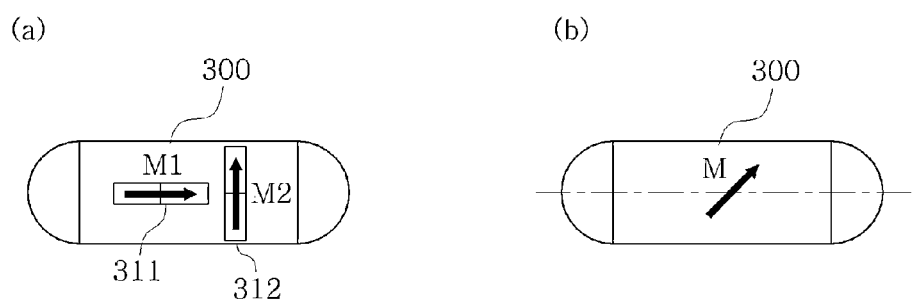

FIGS. 6(a) and 6(b) show an example to make the capsule endoscope have magnetization in an arbitrary direction, and the capsule endoscope may use two permanent magnets 311 and 312 arranged at right angles to each other.

As shown in FIG. 6(a), the capsule endoscope 300 has magnetizations M1 and M2 and includes the two permanent magnets 311 and 312 arranged at right angles to each other. Such an arrangement of the permanent magnets is determined by the two magnetizations M1 and M2 to form magnetization M of a fixed angle to the length direction.

Referring to FIG. 1, the control unit 200 includes a coil controller 220 which controls the sizes and directions of electric currents supplied to the first and second coil units 110 and 120 of the magnetic field generating portion 100 to control operation of the capsule endoscope 300. In this instance, the coil controller 220 controls operation of the coil driving portion 130 to control the direction of the gradient magnetic field of the second coil unit 120.

Moreover, the control unit 200 includes an image receiver 210 which receives an image signal transmitted from the capsule endoscope 300 and a power supply 230 for supplying an operation power of the control unit 200.

In this embodiment, the first and second coil units 110 and 120 and the coil driving portion 130 are controlled by one coil controller 220, but may be controlled by additional dedicated control modules according to speeds or properties of processing data.

Not mentioned in this embodiment in detail, but the control unit may additionally include well-known peripheral devices, such as a capsule endoscope position tracking device which can track the position of the capsule endoscope using X rays, a display for outputting image information receiving from the image receiver 210, or others.

In the capsule type endoscope system according to the present invention, the capsule endoscope 300 by the rotating magnetic field generated from the fixed first coil unit 110 moves while carrying out precession and the spiral motion along the tubular organ by the gradient magnetic field generated by the second coil unit 120, and obtains necessary image information while moving. Hereinafter, the operation of the capsule type endoscope system will be described in detail.

In this embodiment, the first coil unit 110 has the Helmholtz coils disposed on three axes which are at right angles to each other, and the second coil unit 120 has the Maxwell coils.

Figure 7:
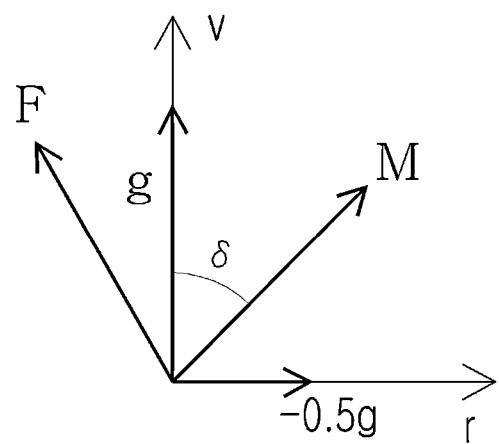
FIG. 7 is a view explaining translation of the capsule endoscope of the capsule type endoscope system according to the preferred embodiment of the present invention.

As shown in FIG. 7, the axial direction of the capsule endoscope is called v. When a gradient magnetic field is generated using MC located on the v axis, a magnetic field having a slope size of g in the v-axis direction and a magnetic field having a slope of $-0.5\,g$ in the radial direction are generated.

In this instance, in the capsule endoscope, a magnetic force is generated by the gradient magnetic field, and the size of the magnetic force is obtained through the following [Math formula 1].

$$F_v = MV_g \sin \delta$$

$$F_r = -0.5 MV_g \cos \delta \qquad \text{[Math formula 1]}$$

In the math formula 1, M is magnetization intensity of the magnet contained in the capsule endoscope, V is volume of the magnet, g is a slope generated by MC, and $\delta$ is an angle between the axial vector v and the magnetization intensity M.

As shown in FIG. 7, the capsule endoscope in such a condition carries out translation in the diagonal direction because a magnetic force F having a fixed angle with the v axis in a v-r plane, and the direction of the force (movement direction) will be changed by the magnetization direction through arrangement of the magnets of the capsule endoscope, namely, by $\delta$.

Figure 8:
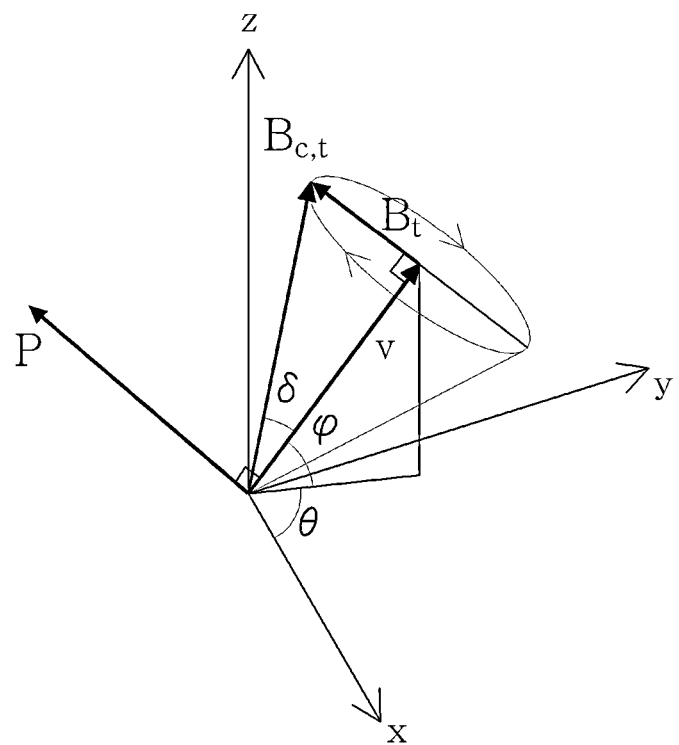
FIG. 8 is a view explaining precession of the capsule endoscope of the capsule type endoscope system according to the preferred embodiment of the present invention.

Next, referring to FIG. 8, in order to make precession with the magnetization direction which is inclined at the angle $\delta$ because the central axis of the capsule endoscope is located on the v axis, it is necessary to properly determine the direction and the size of the magnetic field of the Helmholtz coils to generate a rotating magnetic field.

In FIG. 8, v is a rotational central axis, P is a normal vector (v-z plane) of the rotational central axis, $\varphi$ is an angle between the vector v and the x-y plane when the vector v is projected onto the x-y plane, and $\theta$ is an angle between the vector v and the x axis when the vector v is projected onto the x-y plane.

Referring to FIG. 8, the magnetization direction of the capsule endoscope rotates on the v axis, and when electric currents are applied to the Maxwell coils located on the v axis, the capsule endoscope generates a magnetic force in the v-axis direction and a magnetic force in the r-axis direction (See FIG. 7) at the same time. By a resultant force of the two magnetic forces, the capsule endoscope can carry out the spiral motion by the rotation and the diagonal translation.

In the meantime, in order to make the capsule endoscope carry out the spiral motion along the tubular organ inside a three-dimensional space, the following must be satisfied. First, referring to FIG. 8, the magnetic field that must be generated from each Helmholtz coil for the precession of the capsule endoscope can be expressed by the following [Math formula 2].

$$B_{c,x,t} = a(\cos \varphi \cos \theta) + b(-\sin \varphi \cos \theta \cos 2\pi\omega t + \sin \theta \sin 2\pi\omega t)$$

$$B_{c,y,t} = a(\cos \varphi \sin \theta) + b(-\sin \varphi \sin \theta \cos 2\pi\omega t - \cos \theta \sin 2\pi\omega t)$$

$$B_{c,z,t} = a(\sin \varphi) + b(\cos \varphi \cos 2\pi\omega t) \qquad \text{[Math formula 2]}$$

In the Math formula 2, a and b are $M \cos \delta$ and $M \sin \delta$, and $\omega$ indicates rotational frequencies.

Next, the v axis and the Maxwell coils must be coincided with each other. When the v axis and the Maxwell coils are coincided with each other in direction, the capsule endoscope can easily carry out the spiral motion just by controlling the intensity and the direction of the electric currents applied to the Maxwell coils.

Figure 9:
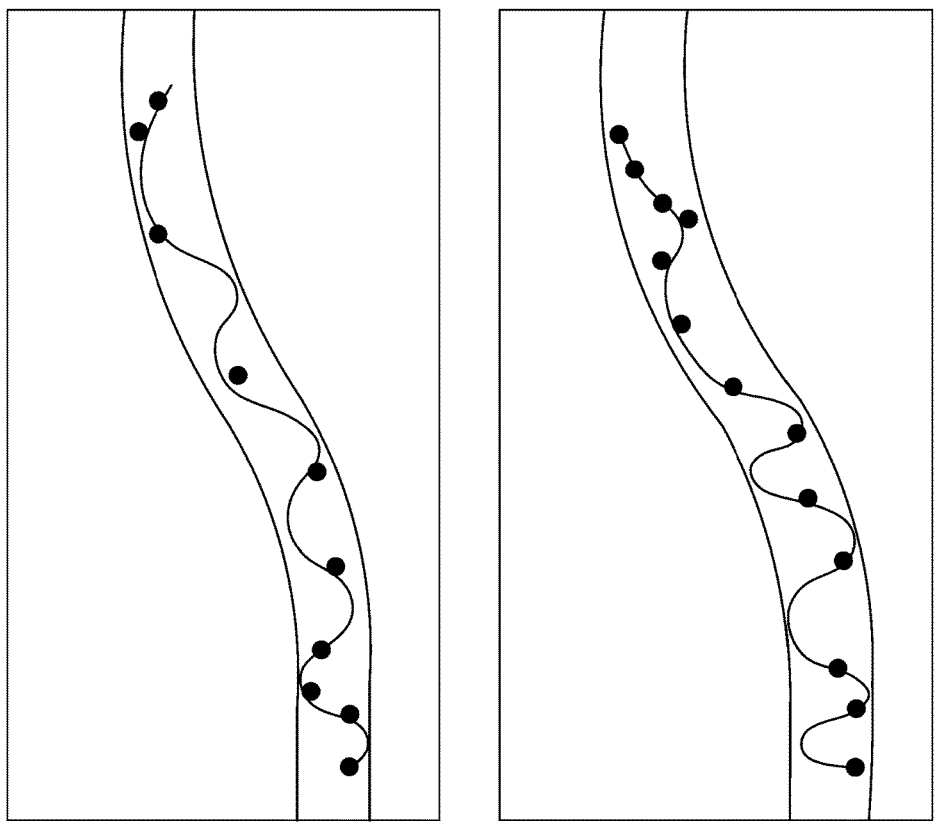
FIG. 9 is a photograph showing an example of operation of the capsule type endoscope system according to the preferred embodiment of the present invention.

FIG. 9 is a photograph showing an example of operation of the capsule type endoscope system according to the present invention. In FIG. 9, the permanent magnets come into contact with the wall surface of a glass tube by the rotating magnetic field and the gradient magnetic field generated from three pairs of the Helmholtz coils and a pair of the Maxwell coils so as to cause the spiral motion in the vertical direction.

It will be understood by those of ordinary skill in the art that there is no intent to limit example embodiments of the invention to the particular forms disclosed and that various changes, modifications and equivalences may be made therein without departing from the spirit and scope of the present invention as defined by the following claims.

What is claimed is:

1. An operation control system of a capsule type endoscope comprising:
   a first coil unit including
      a first coil pair fixed toward an x-axis direction,
      a second coil pair fixed toward a y-axis direction, and
      a third coil pair fixed toward a z-axis direction,
         wherein the x-axis, the y-axis and the z-axis are perpendicular to each other and said first, second and third coil pairs generate magnetic fields in corresponding axis directions, respectively;
   a second coil unit including
      a fourth coil pair opposingly arranged on opposite sides of the first coil unit to surround the first coil unit;

a coil driving unit including
- a rotating arm configured to rotate on a central axis thereof, and
- a movable arm configured to move on the rotating arm and supporting the second coil unit,
- wherein the second coil unit is configure to rotate in certain two directions by the rotating arm and the movable arm, thereby generating a gradient magnetic field in any direction relative to the magnetic fields generated by the first coil unit; and a control unit including
- an image receiver which receives an image signal transmitted from a capsule endoscope, and
- a coil controller which controls electric currents supplied to the first and second coil unit and controls operation of the coil driving unit,
- wherein the capsule endoscope carries out precession by the magnetic fields generated by the first coil unit and a spiral motion along a tubular organ by the gradient magnetic field generated by the second coil unit.

2. The operation control system according to claim 1, wherein the coil driving unit controls the second coil unit to perform three-dimensional rotation by two axis rotating or moving independently from each other.

3. The operation control system according to claim 1, wherein each of the coil pairs of the first coil unit includes a Helmholtz coil.

4. The operation control system according to claim 1, wherein the second coil unit includes a Maxwell coil.

5. A capsule type endoscope system comprising the operation control system according to claim 1, wherein the capsule endoscope has magnetization inclined within a range of an acute angle ($0<\delta<90°$) relative to the length direction of a housing of the capsule endoscope and includes a camera module to capture an image and transmit the image to the outside.

6. A capsule type endoscope system comprising the operation control system according to claim 2, wherein the capsule endoscope has magnetization inclined within a range of an acute angle ($0<\delta<90°$) relative to the length direction of a housing of the capsule endoscope and includes a camera module to capture an image and transmit the image to the outside.

7. A capsule type endoscope system comprising the operation control system according to claim 3, wherein the capsule endoscope has magnetization inclined within a range of an acute angle ($0<\delta<90°$) relative to the length direction of a housing of the capsule endoscope and includes a camera module to capture an image and transmit the image to the outside.

8. A capsule type endoscope system comprising the operation control system according to claim 4, wherein the capsule endoscope has magnetization inclined within a range of an acute angle ($0<\delta<90°$) relative to the length direction of a housing of the capsule endoscope and includes a camera module to capture an image and transmit the image to the outside.

* * * * *